United States Patent [19]

Brorsson et al.

[11] Patent Number: 4,536,201
[45] Date of Patent: Aug. 20, 1985

[54] SYSTEM FOR VENTING GASES IN FLUIDS PASSING THROUGH A CONDUIT

[75] Inventors: Fritz L. Brorsson, Flyinge; Bengt A. G. Dahlberg, Lund; Bengt M. Holmberg, Bjarred, all of Sweden

[73] Assignee: Gambro Lundia AB, Sweden

[21] Appl. No.: 603,309

[22] Filed: Apr. 24, 1984

[30] Foreign Application Priority Data

Nov. 29, 1983 [SE] Sweden .................................. 8306573

[51] Int. Cl.³ .............................................. B01D 19/00
[52] U.S. Cl. ........................................ 55/189; 55/205; 210/257.2; 210/436
[58] Field of Search ................. 55/159, 165, 205, 168, 55/189; 210/96.2, 188, 321.3, 436, 257.2

[56] References Cited

U.S. PATENT DOCUMENTS

| | | | |
|---|---|---|---|
| 3,282,036 | 11/1966 | Griffo et al. | 55/205 X |
| 4,158,034 | 6/1979 | Riede et al. | 210/321.3 X |
| 4,162,974 | 7/1979 | Pernic | 210/321.3 X |
| 4,298,357 | 11/1981 | Pernic | 55/165 |
| 4,366,051 | 12/1982 | Fischer | 210/96.2 |

Primary Examiner—Charles Hart
Attorney, Agent, or Firm—Lerner, David, Littenberg, Krumholz & Mentlik

[57] ABSTRACT

An apparatus as disclosed for the venting of gases contained in fluids passing through a primary conduit in connection with medical treatments comprising throttling means interposed in the primary conduit, pump means downstream of the throttling means for drawing the fluid through said primary conduit, means for enhanced bubble formation in the fluid positioned between the throttling means and pump means in the primary conduit, and venting means disposed in the primary conduit downstream of the pump means, the venting means for removing gaseous bubbles from the fluid when the fluid is passed therethrough.

15 Claims, 6 Drawing Figures

SYSTEM FOR VENTING GASES IN FLUIDS PASSING THROUGH A CONDUIT

FIELD OF THE INVENTION

The present invention relates to a system for venting gases in fluids through a primary conduit and, more particularly, the present invention relates to the venting of gases of a fluid in connection with an expansion chamber position in series with a venting chamber.

BACKGROUND OF THE INVENTION

It is known that during the preparation of a dialysis solution and prior to feeding of the solution to a dialyser, it is first necessary to vent such fluid to remove the air contained therein.

There is disclosed in the U.S. Pat. Nos. 4,158,034 and 4,293,409 a system for venting a fluid in connection with the preparation of a fluid for dialysis. The venting is accomplished in a main duct wherein the liquid is made to pass through a throttling means, then a pump, and finally a venting chamber, from the top of which air is expelled. A known disadvantage of the system arises in that venting will depend to some extent on the existing flow conditions of the fluid. If the flow of the fluid changes rapidly, there is a danger that an adjustment of the venting would not be able to occur equally as rapidly.

SUMMARY OF THE INVENTION

In accordance with the present invention, it has been discovered that these disadvantages can be overcome by an apparatus for the venting of gases contained in fluids passing through a primary conduit in connection with medical treatments comprising throttling means interposed in the primary conduit, pump means downstream of the throttling means for drawing the fluid through the primary conduit, means for enhanced bubble formation in the fluid positioned between the throttling means and the pump means in the primary conduit, and venting means disposed in the primary conduit downstream of the pump means, the venting means for removing gaseous bubbles from the fluid when the fluid is passed therethrough.

In accordance with a further embodiment of the present invention the means for enhanced bubble formation comprises an expansion chamber having an inlet port and an outlet port, the inlet port being positioned lower in the expansion chamber than the outlet port.

In accordance with another embodiment of the apparatus for venting gases, the apparatus further comprises a non-return valve positioned in the primary conduit downstream of the outlet port from the expansion chamber.

In accordance with a preferred embodiment of the present invention for venting gases contained in fluids, the apparatus further comprises a shunt conduit in fluid communication with the expansion chamber and the primary conduit.

In accordance with the preferred embodiment discussed above, further comprising a valve positioned on the shunt conduit adapted to close the shunt conduit at a negative working pressure and open when the negative pressure rises to nominally lower values.

In accordance with another embodiment of the apparatus of present invention, the valve is comprised of a compressible tube, which tube is compressed together to close the shunt conduit at normal working pressure.

In accordance with another embodiment of the preferred embodiment of the apparatus of the present invention discussed above, the embodiment further comprising a pinch device positioned on the compressible tube, the pinch device capable of entirely collapsing the compressible tube at normal working pressure.

In accordance with another embodiment of the present invention for venting gases in a primary conduit wherein the venting means comprises a venting chamber having an inlet port and outlet port, the inlet port being positioned higher in the venting chamber than the outlet port.

In accordance with another embodiment of the present invention as discussed above, wherein the inlet port is positioned tangentially with respect to the venting chamber.

In accorandance with another embodiment of the present invention wherein the outlet port is positioned tangentially in counter-current to a vortex formation of the fluid produced by the inlet port.

In accordance with a preferred embodiment of the present invention wherein the venting chamber is provided with a venting outlet positioned at the highest point of the venting chamber for emitting gases contained in the venting chamber, and a float valve positioned in the venting chamber to prevent the fluid from being sucked out through the venting outlet.

In accordance with another embodiment of apparatus of the present invention, wherein the throttling means positioned upstream of the expansion chamber is adjustable.

In accordance with another embodiment of the preferred embodiment of the apparatus of the present invention discussed above, further comprising a suction pump means positioned downstream from the venting chamber for evacuating a dialysis system of all fluid contained therein.

BRIEF DESCRIPTION OF THE DRAWINGS

The invention will be described in further detail with reference to the attached drawings, which show the use of a preferred embodiment of the invention, and which.

DETAILED DESCRIPTION OF THE INVENTION

Figure 1:
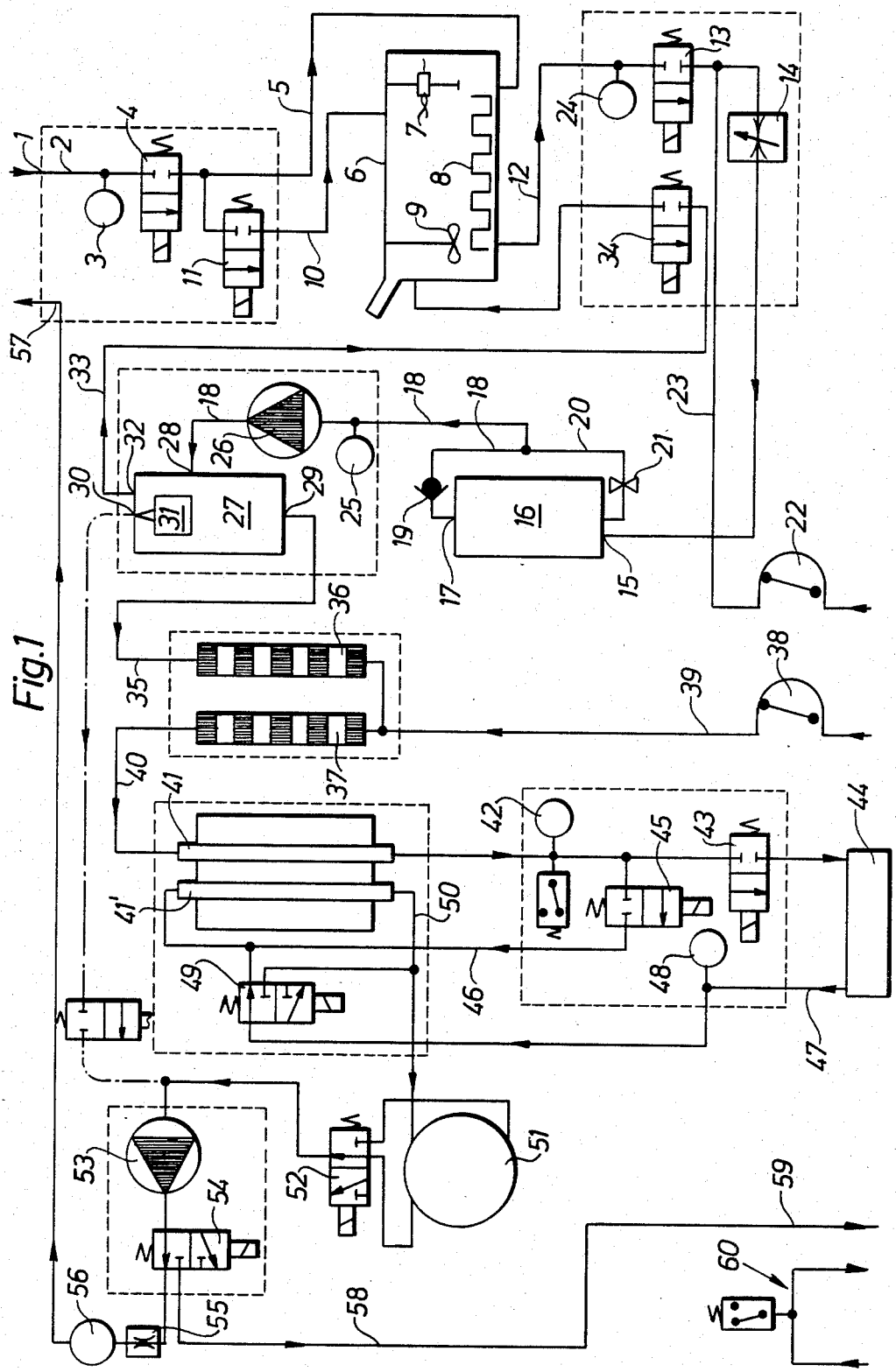
FIG. 1 is a schematic representation of the apparatus of the present invention.

The present invention will be discussed in more detail with reference to FIG. 1 and more specifically with respect to a dialysis system, where there is shown inlet 1 for introducing water into a system through duct 2 having a temperature measuring instrument 3 and an inlet valve 4. Upon leaving inlet valve 4, water flows through duct 5 to a heating vessel 6 having a level control float 7, a heating coil 8 and a stirrer 9. Alternatively, the water passing through inlet valve 4 can be shunted from duct 5 through duct 10 through valve 11 to allow a greater flow of water into vessel 6 for the purpose of rinsing vessel 6 in connection with sterilization of vessel 6.

From vessel 6, water is conducted via duct 12 past a temperature sensor 24 through flow valve 13. Dialysis concentrate drawn up by pump 22 from a source of concentrate and fed through duct 23 is received in duct 12 to be mixed with the water emitting from flow valve 13.

The mixture of water and concentrate is then passed through a adjustable second flow valve or throttling means 14 to be carried to expansion chamber 16. Expansion chamber 16 is provided with an inlet port 15 and an outlet port 17. Inlet port 15 is preferably positioned at the base of expansion chamber 16 and outlet port 17 is positioned at a point higher in expansion chamber 16 than inlet port 15. As a result of this orientation, expansion chamber 16 provides enhanced bubble formation in the water and concentrate mixture. The mixture of water and concentrate and air exit expansion chamber 16 through outlet port 17 into duct 18. Duct 18 is provided with a non-return valve 19, downstream of outlet port 17 of expansion chamber 16.

Figure 4:
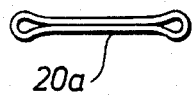
FIG. 4 is a cross-sectional review of a compressible tube in the closed position under normal working pressure utilized in the present invention.
Figure 5:
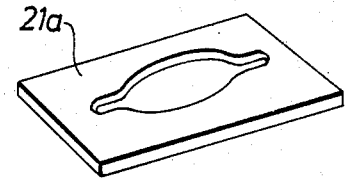
FIG. 5 is a perspective view of a pinch device utilized in the present invention.
Figure 6:
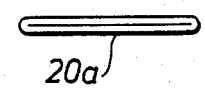
FIG. 6 is a cross-sectional view of the compressible tube shown in FIG. 4 when the pinch device of FIG. 5 is utilized.

Parallel with expansion chamber 16 is shunt line 20, which is in fluid communication with duct 18 and expansion chamber 16. Shunt line 20 can be provided with valve 21 to control the regulation of flow through shunt line 20. Shunt line 20 can also be a compressible tube 20a which serves as a valve under normal working pressure. That is, when there is a partial vacuum in the system, compressible tube 20a collapses, as shown in FIG. 4, closing shunt line 20. However, as also shown in FIG. 4 when compressible tube 20a is in a collapsed state, compressible tube 20a remains partially open at its ends. To overcome this problem one can utilize a pinch device 21a as shown in FIG. 5, whereby compressible tube 20a is inserted within the orifice of pinch device 21a such that the ends of tube 20a are fully compressed together as shown in FIG. 6. The purpose of shunt line 20 will be further detailed with respect to another aspect of the present invention.

Upon leaving expansion chamber 16 the water and concentrate is conducted via duct 18 through pressure gauge 25 by means of suction pump 26 to venting chamber 27.

Figure 2:
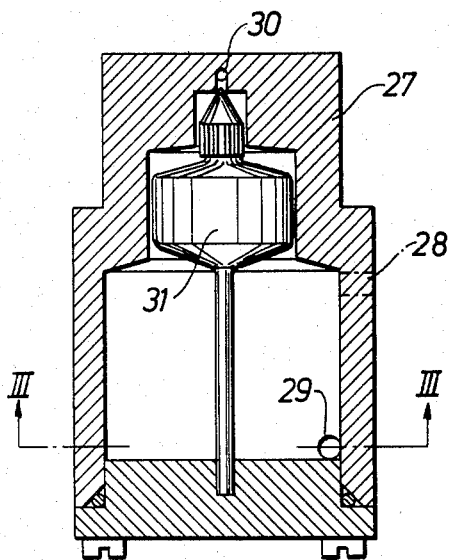
FIG. 2 is a vertical-sectional view of the venting chamber utilized in the present invention.
Figure 3:
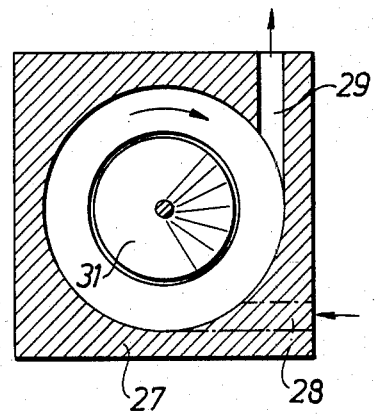
FIG. 3 is a cross-sectional view taken on the line III—III of FIG. 2 looking in the direction of the arrows showing the positioning of the inlet port and outlet port of the venting chamber utilized in the present invention.

Venting chamber 27 as shown more specifically in FIG. 2 is provided with an inlet port 28 and an outlet port 29. Inlet port 28 is positioned tangentially to the chamber and higher in venting chamber 27 than outlet port 29. In operation, outlet port 29 is also positioned tangentially with respect to the chamber in counter-current to the vortex formation produced by the flow of the mixture through inlet port 28 as shown in FIG. 3.

Venting chamber 27 is also provided with a second outlet port 30 for emitting the gases vented from the mixture of water and concentrate. Contained within venting chamber 27 is float 31 which causes outlet port 30 to close when the level of fluid within the venting chamber 27 rises to a point where there would be a risk of the fluid being sucked out through outlet port 30.

The mixture of water and concentrate exits through outlet port 29 into duct 35 to be carried through the rest of the dialysis system. Alternatively, if the dialysis system is being sterilized as described in U.S. Pat. No. 4,158,034, the sterilization fluid is drawn out through a third outlet port 32 positioned at the top of venting chamber 27 via duct 33 through valve 34 to return to heating vessel 6.

During dialysis, the fluid mixture is conducted via duct 35 to conductivity meter 36. If a second concentrate is to be added to the mixture of water and concentrate, the second concentrate is fed into duct 35 from a source of second concentrate by means of pump 38 through duct 39. Following this addition of second concentrate, the total liquid mixture is passed again through a second conductivity meter 37. Upon exiting from conductivity meter 37 into duct 40 the liquid is introduced into flow meter 41. From flow meter 41, the temperature of the total liquid mixture is measured by temperature measuring instrument 42, and if the temperature condition is acceptable, the total liquid mixture flows through valve 43 to dialyser 44.

If it is determined after measurement that the temperature or the conductivity of the total liquid mixture of fluid is not of a desired value, valve 43 to dialyser 44 closes and the total liquid mixture is then conducted through valve 45 into duct 46 bypassing dialyzer 44 to a second conduit 41' in the aforementioned flow meter 41.

If the total liquid mixture has the desired characteristics and is passed through dialyser 44, the mixture exits dialyser 44 via duct 47 through pressure guage 48 and valve 49 to conduit 41' in flow meter 41. The liquid is then conducted through duct 50 to a blood leakage dectector 51 and valve 52 to suction pump 53. Suction pump 53 serves to draw the total liquid mixture through dialyser 44.

From pump 53 the liquid is then conducted through outlet valve 54 through throttling means 55, safety control meter 56 for ph measurement to outlet 57. Alternately, when the system is utilized in sequence dialysis or if a waste liquid is to be flushed from the system, the ultrafiltrate removed or the waste liquid may be passed through valve 54 via duct 58 to a collection point 59 for such filtrate or waste liquid.

A safety bypass 60 can be utilized in connection with the sterilization of the system. The safety bypass is further described in more detail in U.S. Pat. No. 4,122,010.

Pumps 26 and 53 can be used to expurgate the entire system of all fluid by feeding air into the system via heating vessel 6. The pressure in the system will drop when the air reaches the throttling means 14 thereby generating a pressure through the system of a nominally lower value through the introduction of air into the system, the change of pressure in the system will cause compressible tube 20a to open to allow the efficient emptying of expansion chamber 16.

The system described hereinabove is also utilizable in connection with venting of a replacement liquid for hemofiltration or plasmaphoreisis or for venting of liquids in general.

Naturally, the invention is not limited solely to the embodiment described above, but may be modified within the scope of the following claim.

What is claimed is:

1. An apparatus for the venting of gases contained in the fluid passing through a primary conduit in connection with medical treatments comprising:

throttling means interposed in said primary conduit;
pump means downstream of said throttling means for drawing said fluid through said primary conduit;

means for enhanced bubble formation in said fluid positioned between said throttling means and pump means in said primary conduit;

a shunt conduit in fluid communication with said means for enhanced bubble formation and said primary conduit; and venting means disposed in said primary conduit downstream of said pump means, said venting means for removing gaseous bubbles from said fluid when said fluid is passed therethrough.

2. The apparatus for the venting of gases as defined in claim 1, wherein said means for enhanced bubble formation comprises an expansion chamber having an inlet port and an outlet port, said inlet port positioned lower in said expansion chamber than said outlet port.

3. The apparatus for the venting of gases as defined in claim 2, further comprising a non-return valve positioned in said primary conduit downstream of said outlet port from said expansion chamber.

4. The apparatus for venting of gases as defined in claims 2 or 3, wherein said shunt conduit is in fluid communication with said expansion chamber at a point in said expansion chamber capable of emptying said expansion chamber of said liquid.

5. The apparatus for venting of gases as defined in claims 2 or 3, further comprising a valve positioned on said shunt conduit adapted to close said shunt conduit at a negative working pressure and open when said negative pressure rises to nominally lower values.

6. The apparatus for venting gases as defined in claim 5, wherein said valve is comprised of a compressible tube, said tube being compressed together to close said shunt conduit at normal working pressure.

7. The apparatus for venting of gases as defined in claim 6, further comprising a pinch device positioned on said compressible tube, said pinch device capable of entirely collapsing said compressible tube at normal working pressure.

8. The apparatus for venting of gases as defined in claim 1, wherein said venting means comprises a venting chamber having an inlet port and an outlet port, said inlet port being positioned higher in said venting chamber than said outlet port.

9. The apparatus for venting of gases as described in claim 8, wherein said inlet port is positioned tangentially with respect to said venting chamber.

10. The apparatus for venting of gases as described claim 9, wherein said outlet port is positioned tangentially in countercurrent to a vortex formation of the fluid produced by said inlet port.

11. The apparatus for venting of gases as defined in claim 1, wherein said venting chamber is provided with a venting outlet positioned at the highest point of said venting chamber for emitting gases contained in said chamber, and a float valve positioned in said venting chamber to prevent said fluid from being sucked out through said outlet.

12. The apparatus for venting gases as defined in claim 1, wherein said throttling means is adjustable.

13. The apparatus for venting of gases from a liquid as defined in claim 1, further comprising a suction pump means positioned downstream from said venting chamber.

14. The apparatus for venting of gases from a liquid as defined in claim 12, wherein said suction pump means downstream from said venting chamber draws said liquid through said shunt conduit when said negative pressure in said system is of a nominally lower value.

15. An apparatus for the venting of gases contained in a fluid passing through a primary conduit in connection with medical treatments comprising:

throttling means interposed in said primary conduit;

pump means downstream of said throttling means for drawing said fluid through said primary conduit;

an expansion chamber having an inlet port and an outlet port, said expansion chamber positioned between said throttling means and pump means in said primary conduit;

a shunt conduit in fluid communication with said expansion chamber, said shunt conduit connected at a point in said expansion chamber capable of emptying said expansion chamber of said liquid in said primary conduit in cooperation with said pump means; and venting means disposed in said primary conduit downstream of said pump means, said venting means for removing gaseous bubbles from said fluid when said fluid is passed therethrough.

* * * * *